United States Patent [19]

Ward et al.

[11] Patent Number: 5,166,136
[45] Date of Patent: Nov. 24, 1992

[54] SPIROLACTAM CONTAINING PEPTIDES

[75] Inventors: Peter Ward, Pinner; George B. Ewan, Bucks, both of England

[73] Assignee: Glaxo Group Limited, London, England

[21] Appl. No.: 384,685

[22] Filed: Jul. 25, 1989

[30] Foreign Application Priority Data

Jul. 25, 1988 [GB] United Kingdom ............... 8817711
Mar. 8, 1989 [GB] United Kingdom ............... 8905286

[51] Int. Cl.$^5$ .................. A61K 37/02; C07K 5/08; C07K 5/10; C07K 7/06
[52] U.S. Cl. .......................... 514/15; 514/16; 514/17; 514/18; 514/19; 530/328; 530/329; 530/330; 530/331
[58] Field of Search ................ 514/15-19; 530/328-331

[56] References Cited

U.S. PATENT DOCUMENTS 4,680,283 7/1987 Veber et al. .................. 514/17

FOREIGN PATENT DOCUMENTS 0176436 4/1986 European Pat. Off. .
0336230 10/1989 European Pat. Off. .
2216529A 10/1989 United Kingdom .

OTHER PUBLICATIONS

Hinds et al., "Peptide Analogues in Studies of Antibody-Antigen Binding": Synthesis and Computer Modelling of a Peptide Antigen Containing a β-Bend Mimic, Sep., 1987.

Primary Examiner—Lester L. Lee
Attorney, Agent, or Firm—Bacon & Thomas

[57] ABSTRACT

These are described spirolactam derivatives of formulae (Ia) and (Ib)

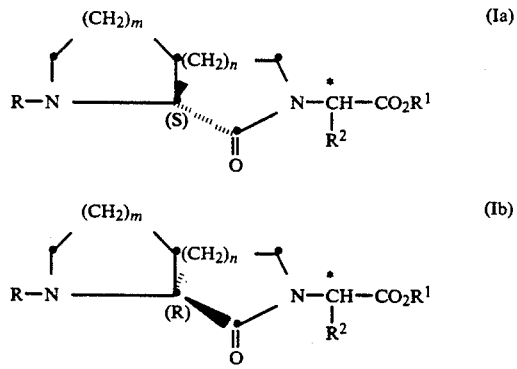

wherein
R represents a hydrogen atom or a conventional nitrogen protecting group;
$R^1$ represents a hydrogen atom or a conventional carboxyl protecting group or activating group;
$R^2$ represents the side chain of any naturally occurring amino acid;
m represents 1 or 2;
n represents 1 or 2;
the confirguration at * may be (R) or (S) or a mixture thereof; with the proviso that when R represents the nitrogen protecting group $R^3$—CO(O)— (where $R^3$ represents $(CH_3)_3C$—), the group —$CO_2R^1$ represents the protected carboxy group —$CO_2CH_3$, m is 1 and n is 1 in the compounds of formula (Ib); $R^2$ may not represent an arylmethyl group;
and solvates or acid addition salts thereof.

These derivatives are of value in the preparation of spirolactam compounds which, depending on their stereochemistry, are either antagonists or agonists of substance P, and as such have a variety of therapeutic properties.

3 Claims, No Drawings

SPIROLACTAM CONTAINING PEPTIDES

This invention relates to spirolactam derivatives, to processes for their preparation and to their use in the preparation of therapeutically useful peptides.

Substance P is an endogenous undecapeptide amide and a putative neurotransmitter/neuromodulator of mammalian central nervous systems having the following structural formula:

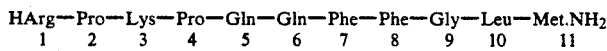

Analogues of substance P, or its C-terminal fragments, containing multiple D-amino acid substituents, principally in positions 7, 9 and 10, have been described in the literature. Such compounds are claimed to antagonise the effects of substance P and related peptides acting at neurokinin receptors in vitro and in vivo.

Antagonists of substance P have been reported to be useful as analgesics and anti-inflammatories. Such compounds may also be of use as anti-psoriatics, anti-psychotics, anti-asthmatics and anti-diarrhoeals.

We have found that the introduction of a novel spirolactam unit into the peptide chain of substance P and its analogues produces compounds which, depending on their sterochemistry, are either antagonists or agonists of substance P. The antagonists of substance P have a particularly advantageous profile of activity in that they are highly potent and selective at certain specific neurokinin receptors. The agonists of substance P have substance P like activity but have relative selectivity for certain specific neurokinin receptors.

Thus, according to one aspect of the present invention, we provide the spirolactam derivatives of formulae (Ia) and (Ib)

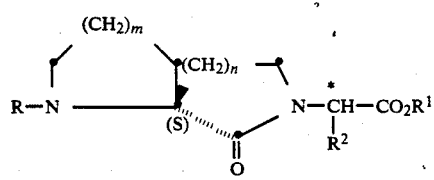

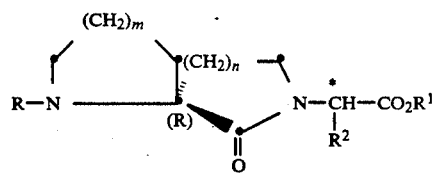

wherein
R represents a hydrogen atom or a conventional nitrogen protecting group;
$R^1$ represents a hydrogen atom or a conventional carboxyl protecting group or activating group;
$R^2$ represents the side chain of any naturally occurring amino acid;
m represents 1 or 2;
n represents 1 or 2;
the configuration at * may be (R) or (S) or a mixture thereof; with the proviso that when R represents the nitrogen protecting group $R^3$—CO(O)— (where $R^3$ represents $(CH_3)_3C$—), the group —$CO_2R^1$ represents the protected carboxy group —$CO_2CH_3$, m is 1 and n is 1 in the compounds of formula (Ib); $R^2$ may not represent an arylmethyl group;
and salts and solvates thereof.

In one aspect the invention provides compounds of formulae (Ia) and (Ib) in which $R^2$ and n and m are as defined in formulae (Ia) and (Ib) and R and $R^1$ are hydrogen atoms or more particularly protecting groups.

In the general formulae (Ia) and (Ib), when R represents a nitrogen protecting group this may be for example a nitrogen protecting group useful in conventional peptide synthesis such as an acyl group, for example an acetyl group or an optionally substituted acetyl group (e.g. trifluoroacetyl) or the group $R^3$—OC(O)— (wherein $R^3$ represents for example $Cl_3CCH_2$—, $(CH_3)_3C$—,

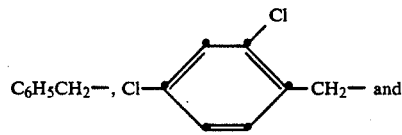

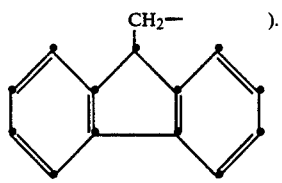

).

In the general formulae (Ia) and (Ib), $R^1$ may represent a carboxyl protecting group which may be for example a carboxyl protecting group useful in conventional peptide synthesis for example the group —$CO_2R^1$ may represent an alkyl or aryl ester in which case $R^1$ may represent a methyl, ethyl, tertbutyl, methoxymethyl, benzyl, diphenylmethyl, triphenylmethyl or a p-nitrobenzyl group.

In the general formulae (Ia) and (Ib) $R^1$ may represent a carboxyl activating group which may be for example a carboxyl activating group useful in conventional peptide synthesis for example the group —$CO_2R^1$ may represent an N-hydroxybenzotriazole or pentafluorophenyl ester.

A preferred group of compounds are those of formulae (Ia) and (Ib) where n and m are 1.

Also preferred are the compounds of formulae (Ia) and (Ib) wherein the group $R^2$ is —$CH_2$—$CH(CH_3)_2$.

It will be appreciated that the compounds of formulae (Ia) and (Ib) according to the present invention may have an (R) or (S) configuration (or a mixture thereof) at the asymmetric centre marked with an asterisk.

Compounds of general formulae (Ia) and (Ib) and salts and solvates thereof may be prepared by the general methods outlined hereinafter. In the following description the groups R, $R^1$ and $R^2$, n and m are as defined for the compounds of general formulae (Ia) and (Ib) unless otherwise stated.

According to a first general process (A) compounds of formulae (Ia) and (Ib) may be prepared by cyclisation of a compound of formula (II)

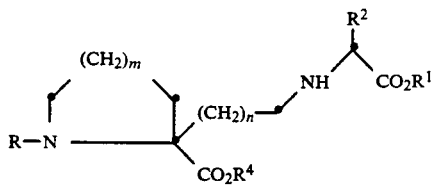

or a protected derivative thereof where $R^4$ represents a hydrogen atom or $C_{1-4}$ alkyl group, optionally in the presence of a cyclisation reagent followed where necessary by deprotection.

Thus, when $R^4$ is hydrogen or an unbranched $C_{1-4}$ alkyl group, cyclisation may take place spontaneously, conveniently in a suitable solvent such as a halogenated hydrocarbon (e.g. dichloromethane) or an alcohol (e.g. methanol) at a temperature in the range of 0°–100° C.

When $R^4$ represents a hydrogen atom cyclisation may conveniently take place in the presence of a suitable cyclisation reagent such as a carbodiimide (e.g. dicyclohexylcarbodiimide or 1-ethyl-3-(3-dimethylaminopropyl)carbodiimide) in a suitable solvent such as a halogenated hydrocarbon (e.g. dichloromethane), an ester (e.g. ethyl acetate) or an ether (e.g. tetrahydrofuran) at a temperature in the range of 0°–30° C. (e.g. 20°–25° C.).

When $R^4$ represents a hydrogen atom or a $C_{1-4}$ alkyl group cyclisation may be effected by base catalysis using a tertiary organic base (e.g. triethylamine) at a temperature ranging from ambient to the reflux temperature of the reaction mixture.

Alternatively when $R^4$ represents a hydrogen atom or an unbranched $C_{1-4}$ alkyl group cyclisation may take place in the presence of an acidic buffer (e.g. an acetate buffer) for example at a pH between 3 and 5, optionally in the presence of a suitable solvent such as an alcohol (e.g. methanol) at a temperature ranging from ambient to the reflux temperature of the solvent.

Compounds of general formula (II) may be obtained by reduction of the imines of formula (III)

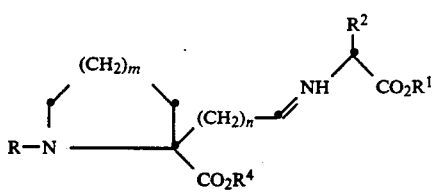

or a protected derivative thereof where $R^4$ is hydrogen, or a group convertible thereto (e.g. a benzyl group) or a $C_{1-4}$ alkyl group followed where necessary by deprotection.

Suitable reducing agents include alkali metal hydrides such as sodium borohydride or sodium cyanoborohydride. The reduction conveniently takes place in a suitable solvent such as an alcohol (e.g. methanol or ethanol) or a mixture of an alcohol and an ether (e.g. tetrahydrofuran) at a temperature in the range of 0°–30° C. (e.g. 20°–25° C.).

Alternatively, compounds of formula (III) may be reduced by catalytic hydrogenation using a metal catalyst such as palladium-on-carbon in the presence of a suitable solvent such as an alcohol (e.g. methanol or ethanol) or an ester (e.g. ethyl acetate).

Compounds of formula (III) where n is 1, R is a protecting group and $R^4$ is hydrogen may be obtained by condensation of a compound of formula (IV)

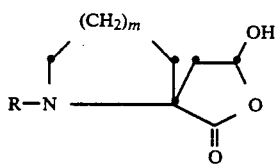

where R is a protecting group with a compound of formula (V)

where R1 is a protecting group (e.g. $C_{1-4}$alkyl) and the configuration at * is as defined above followed where necessary by deprotection.

Condensation conveniently takes place in the presence of a suitable solvent such as an alcohol (e.g. methanol or ethanol) or an ether (e.g. tetrahydrofuran) or a mixture thereof at a temperature in the range of 0°–30° C. (e.g. 20°–25° C.).

Alternatively, compounds of formula (III) where R is a protecting group and $R^4$ is a $C_{1-4}$alkyl or benzyl group may be prepared by condensation of the compounds of formula (V) with the aldehydes of formula (VI)

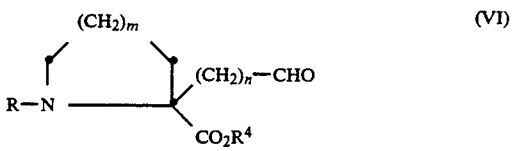

where R is a protecting group and $R^4$ is a $C_{1-4}$alkyl or benzyl group, conveniently in the presence of a suitable solvent such as an ether (e.g. tetrahydrofuran) at a temperature in the range of 0°–30° C. (e.g. 20°–25° C.), followed where necessary by deprotection.

Compounds of formula (IV) may be obtained as a result of spontaneous cyclisation of the compounds of formula (VI) where $R^4$ is hydrogen optionally in the presence of a suitable solvent.

Compounds of formula (VI) where $R^4$ is hydrogen or a $C_{1-4}$alkyl or benzyl group may be obtained by ozonolysis of the alkenes of formula (VII)

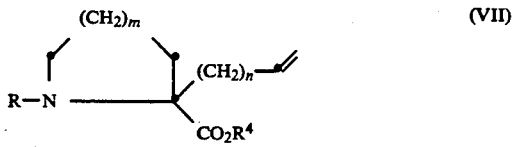

where R is a protecting group and $R^4$ is hydrogen or a $C_{1-4}$alkyl or benzyl group, by treating compounds of formula (VII) with ozone conveniently in a suitable solvent such as a chlorinated hydrocarbon (e.g. dichloromethane) at a temperature in the range of −70° to −30° C. followed by decomposition of the intermediate ozonide thus formed.

Decomposition of the intermediate ozonide may be effected using a suitable reducing agent such as zinc in acetic acid, trimethyl phosphite, triphenyl phosphine or catalytic hydrogenation.

Alternatively, compounds of formula (VI) where $R^4$ is a $C_{1-4}$alkyl or benzyl group and n is 2 may be obtained from compounds of formula (VII) where $R^4$ is a $C_{1-4}$alkyl or benzyl group and n is 1 by hydroboration-/oxidation followed by further oxidation of the alcohol thus formed.

Hydroboration may be effected using a monoalkylborane (e.g. thexylborane) or a dialkylborane (e.g. disiamylborane) conveniently in a solvent such as an ether (e.g. tetrahydrofuran) at a temperature in the range of $-20°$ to $+30°$ C. (e.g. $0°$ C.).

Oxidation of the thus formed alkylborane may be effected using hydrogen peroxide and sodium hydroxide at a temperature in the range of $0°-+30°$ C.

Oxidation of the thus formed alcohol may be effected using a suitable oxidising agent such as pyridinium chlorochromate or pyridine dichromate in the presence of a suitable solvent such as an ether (e.g. tetrahydrofuran) or using an acid anhydride or acid chloride (e.g. oxalyl chloride) in the presence of a sulphoxide (e.g. dimethylsulphoxide).

Alternatively, the compounds of formula (VI) may be obtained by hydroboration of the compounds of formula (VII) followed by direct oxidation of the thus formed alkylboranes to the aldehydes using pyridinium chlorochromate or pyridine dichromate as described above.

The alkenes of formula (VII) where R is a protecting group and $R^4$ is a $C_{1-4}$alkyl or benzyl group may be obtained by treating the compounds of formula (VIII)

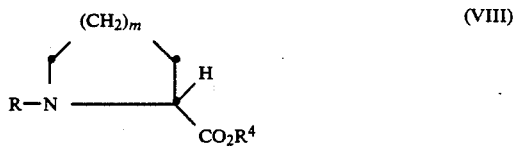

where R is a protecting group and $R^4$ is a $C_{1-4}$alkyl or benzyl group, with a base such as n-butyl lithium conveniently in a solvent or mixture of solvents such as an ether (e.g. tetrahydrofuran) and hexamethyldisilazane at a temperature in the range of $-80°$ to $-30°$ C., followed by treatment with a compound of formula (IX)

where L is a readily displaceable atom or group optionally in a suitable solvent (e.g. tetrahydrofuran) at a temperature in the range of $-80°$ to $-30°$ C.

Suitable compounds of formula (IX) include those wherein L represents for example a halogen atom (e.g. chlorine, bromine or iodine), an acyloxy group or a sulphonyloxy group.

Compounds of formula (VII) where R is a protecting group, $R^4$ is hydrogen and m is 1 may be obtained on hydrolysis of the oxadoladinones of formula (X)

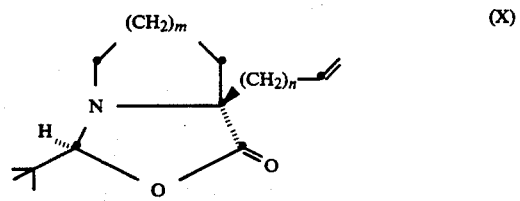

followed by protection of the amino group.

Hydrolysis is conveniently carried out in a suitable solvent such as an aqueous alcohol (e.g. methanol) in the presence of silica gel at a temperature in the range of $0°-30°$ C. (e.g. $20°-25°$ C.).

Compounds of formulae (IX) and (X) are either known compounds or may be prepared using methods analogous to those used for the preparation of known compounds. For example compounds of formula (X) may be prepared by the method of D. Seebach et. al., *J. Amer. Chem. Soc.*, 1983, 105, 5390.

The compounds of formulae (Ia) and (Ib) have at least two centres of asymmetry, namely the spiro-carbon and the carbon marked with an asterisk. It will be appreciated that when process A utilizes the compound of formula (X), compounds of formula (Ia) will be obtained. When process A does not utilize the compound of formula (X) compounds of formulae (Ia) and (Ib) will be obtained either as a mixture of two pairs of enantiomers (i.e. if the amino acid of formula (V) is a mixture of (R) and (S) isomers) or as a mixture of two diastereoisomers (i.e. if a single isomer of the amino acid of formula (V) is used).

Thus, in order to obtain compounds of either formula (Ia) or (Ib), the stereoisomers according to process A may be separated at any convenient point in the reaction scheme by conventional methods (see for example "Stereochemistry of Carbon Compounds" by E. L. Eliel (McGraw Hill 1962)). For example fractional crystallisation or chromatography may be used.

According to another general process (B), a compound of formula (Ia) or (Ib) may be converted into another compound of formula (Ia) or (Ib) using conventional techniques. Such conventional techniques include protection and deprotection for example as described in 'Protective Groups in Organic Synthesis' by Theodora W. Green (John Wiley and Sons, 1981).

Thus, compounds of formula (Ia) or (Ib) where R and/or $R^1$ is/are hydrogen atom(s) may be prepared by deprotection of compounds of formula (Ia) or (Ib) where R and/or $R^1$ is/are protecting groups.

Suitable amine protecting groups for example are those included in the definition of R in formulae (Ia) and (Ib) above.

Suitable carboxyl protecting groups for example are those included in the definition of $R^1$ in formulae (Ia) and (Ib) above.

Thus, N-benzyloxycarbonyl and N-2,4-dichlorobenzyloxycarbonyl groups may be removed by hydrogenolysis in the presence of a metal catalyst (e.g. palladium-on-carbon) conveniently in a solvent such as an alcohol (e.g. methanol) or an ester (e.g. ethyl acetate). Alternatively, N-benzyloxycarbonyl groups may be removed under conditions of acid hydrolysis e.g. using hydrogen bromide in acetic acid. N-t-butoxycarbonyl groups may be removed under conditions of acidic hydrolysis (e.g. hydrochloric acid in acetic acid or dioxan or trifluoroacetic acid with or without a solvent).

9-fluorenylmethyloxcarbonyl groups may be removed in the presence of a base such as an amine (e.g. ammonia, piperidine, morpholine or ethanolamine) optionally in the presence of a solvent such as an amide (e.g. dimethylformamide).

Acetyl protecting groups may be removed under conditions of acidic (e.g. hydrochloric acid) and basic (e.g. potassium hydroxide or ammonia/methanol solution) hydrolysis.

Unbranched alkyl (e.g. methyl) ester groups may be removed under conditions of basic hydrolysis for example using sodium hydroxide in methanol. Tertbutyl and diphenylmethyl ester groups may be removed under conditions of moderate acidic hydrolysis for example using formic or trifluoroacetic acid at room temperature. Benzyl, diphenylmethyl and nitrobenzyl ester groups may be removed by hydrogenolysis in the presence of a metal catalyst (e.g. palladium).

Compounds of formulae (Ia) and (Ib) may be used to prepare peptide analogues which are either antagonists or agonists of substance P. For example compounds of formula (Ia) may be used to prepare antagonists of substance P. Thus, as an illustration to a further aspect of the present invention, compounds of general formula (XI) are provided

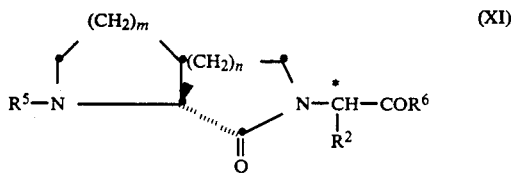

wherein $R^2$, n and m are as defined in formula (Ia) above;

the configuration at * is as defined in formula (Ia) above;

$R^5$ represents a peptide chain, optionally protected at the N-terminal residue, consisting of 2 to 8 amino acid units chosen from L-phenylalanine, D-phenylalanine, L-proline, L-glutamine, L-arginine, L-lysine, L-threonine, L-histidine, L-asparagine, L-methionine, D-methionine, L-alanine, L-serine, L-tyrosine, L-pyroglutamic acid, L-aspartic acid,

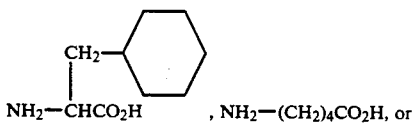

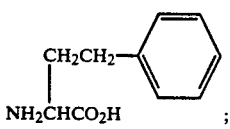

$R^6$ represents an amino acid amide chosen from L-methionyl, D-methionyl, L-phenylalanyl or L-tryptophyl amides, optionally substituted on the amide nitrogen by the group $-CH_2CH_2NH_2$; or the groups

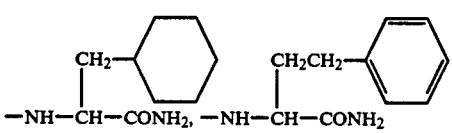

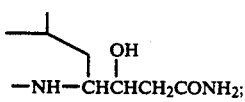

or $R^6$ represents the group

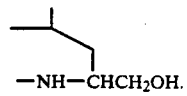

Such compounds are highly potent antagonists to substance P and exhibit a selectivity of action towards $NK_1$ (neurokinin) receptors vs $NK_2$ receptors.

Compounds of formula (XI) have been shown to be antagonists of substance P both in vitro and in vivo.

Substance P agonist and antagonist activity at NK-1 receptors was determined in vitro using guinea-pig ileum longitudinal muscle by measuring the isotonic contractile effect of the test compound either against substance P methyl ester (in the case of antagonists) or against the known antagonists atropine, mepyramine, methysergide and indomethacin (in the case of agonists) for example according to methods described by J. R. Brown, C. C. Jordan, P. Ward and A. R. Whittington in "Tachykinin Antagonists" Ed. R. Hakanson and F. Sundler, (Elsevier Science Publishers B. V., 1985).

Substance P agonist and antagonist activity at NK-2 receptors was determined from in vitro contractile responses of rat colon muscularis mucosae in the presence of the above antagonists or neurokinin A as appropriate.

In vivo substance P antagonist activity was demonstrated in the mouse using the reciprocal hind-limb scratching response test as described by J. K. L. Hylden and G. L. Wilcox in *Brain Research*, 217, (1981), 212-215. Intrathecal administration of substance P, or related compounds such as its C-terminal methyl ester, at the L5-L6 level of the spinal cord in conscious mice produces a characteristic scratching and biting response. Co-administration of the test compounds (intrathecally) inhibited scratching induced by substance P methylester.

Compounds of formula (XI) may therefore be of use as analgesics. They are also potentially useful for the treatment of diseases such as psoriasis, inflammatory and allergic disorders - especially of the eye and skin, diarrhoea and diseases associated with reversible airways obstruction such as asthma and chronic bronchitis. Compounds of formula (XI) may also be of use in the treatment of CNS disorders such as psychosis.

According to a further aspect of the invention we provide a compound of formula (XI) or a physiologically acceptable salt thereof for use in the treatment of the aforementioned diseases.

According to another aspect of the invention we provide the use of a compound of formula (XI) or a physiologically acceptable salt thereof for the manufacture of a therapeutic agent for the treatment of the aforementioned diseases.

According to a further aspect of the invention we provide a method of treating the aforementioned diseases which method comprises administering an effective amount of a compound of formula (XI) or a physiologically acceptable salt thereof to the patient.

It will be appreciated that the compounds of formula (XI) may advantageously be used in conjunction with one or more other therapeutic agents, such as for example antibiotic or antifungal agents. It is to be understood that the present invention covers the use of a compound of formula (XI) or a physiologically acceptable salt thereof in combination with one or more other therapeutic agents.

The compounds of the invention may be formulated in any convenient manner with one or more pharmaceutical carriers. Thus, a further aspect of the invention includes pharmaceutical compositions comprising a compound of formula (XI) or a physiologically acceptable salt thereof formulated for oral, buccal, transdermal, parenteral, implant, topical (including opthalmic and nasal), or rectal administration or in a form suitable for administration by inhalation or insufflation.

For oral administration the pharmaceutical composition may take the form of for example tablets which may be coated by methods well known in the art.

For parenteral administration the compounds of formula (XI) may be given as a bolus injection or by continuous infusion (e.g. via intravenous, intravascular, subcutaneous or intrathecal routes). The compositions may take such forms as suspensions, solutions or emulsions in oily or aqueous vehicles and may contain formulatory agents such as suspending, stabilising and/or dispersing agents. For administration by injection these may take the form of a unit dose presentation or as a multidose presentation preferably with an added preservative.

Alternatively for parenteral administration the active ingredient may be in powder form for reconstitution with a suitable vehicle.

The compounds of formula (XI) may be formulated as ointments and creams for transdermal administration and as suppositories or retention enemas for rectal administration.

For buccal administration the composition may take the form of tablets or lozenges formulated in conventional manner.

For administration by inhalation the compounds according to the invention are conveniently delivered in the form of an aerosol spray presentation from pressurised packs with the use of a suitable propellant, e.g. dichlorodifluoromethane, trichlorofluoromethane, dichlorotetrafluoroethane, carbon dioxide or other suitable gas, or from a nebuliser. In the case of a pressurised aerosol the dosage unit may be determined by providing a valve to deliver a metered amount.

Alternatively, for administration by inhalation the compounds of formula (XI) may take the form of a dry powder composition, for example a powder mix of the compound and a suitable powder base such as lactose or starch. The powder composition may be presented in unit dosage form in, for example, capsules or cartridges of e.g. gelatin, or blister packs from which the powder may be administered with the aid of an inhaler or insufflator.

The compound of formula (XI) may also be formulated as a depot preparation. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

The compounds of formula (XI) may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilised components.

Lotions may be formulated with an aqueous or oily base and will in general also contain one or more emulsifying agents, stabilising agents, dispersing agents, suspending agents, thickening agents, or colouring agents. Drops may be formulated with an aqueous or non aqueous base also comprising one or more dispersing agents, stabilising agents, solubilising agents or suspending agents. They may also contain a preservative.

A proposed daily dosage of active compound for the treatment of man is 0.01 mg/kg to 10 mg/kg, which may be conveniently administered in 1 to 4 doses. The precise dose employed will depend on the age and condition of the patient and on the route of administration. Thus a suitable dose for systemic administration is 0.1 mg/kg is 10 mg/kg and for intrathecal administration 0.01 mg/kg to 1 mg/kg.

According to another aspect of the invention we provide a process (C) for the preparation of the peptide analogues of formula (XI). In the following description R to $R^6$, n and m are as defined in formulae (Ia) and (XI) above.

Thus, the compounds of formula (XI) may be prepared by reacting a compound of formula (XII)

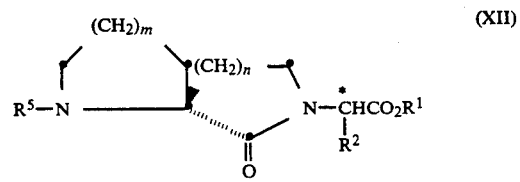

(wherein $R^1$ represents a carboxyl activating group and $R^5$ is a protected peptide chain as defined in formula (XI) above) with an amino compound of formula (XIII)

H—$R^6$ (XIII)

according to conventional methods of peptide synthesis.

Compounds of formula (XII) where $R^1$ is a carboxyl activating group may be prepared from the corresponding compounds of formula (XII) where $R^1$ is a hydrogen atom by methods capable of effecting the conversion. This reaction may optionally be carried out in situ.

Thus, for example a compound of formula (XII) where $R^1$ is a hydrogen atom may be activated in situ to a compound of formula (XII) where $R^1$ is a carboxyl activating group by reaction with an N-hydroxy compound such as N-hydroxybenzotriazole in the presence of a condensing agent such as a carbodiimide (e.g. dicyclohexylcarbodiimide) in a solvent such as an amide (e.g. dimethylformamide) at a temperature in the range of 0°–30° C.

Compounds of formula (XII) where $R^1$ is a carboxyl activating group may be reacted with compounds of formula (XIII) optionally in a solvent such as an amide (e.g. dimethylformamide) at a temperature range of 0°–30° C.

Compounds of formula (XII) wherein $R^1$ is a hydrogen atom may be prepared from compounds of formula (XII) where $R^1$ is a carboxyl protecting group by conventional deprotection methods as used in peptide synthesis, for example those methods described in process (B) hereinbefore.

Compounds of formula (XII) where $R^1$ is a carboxyl protecting group may be prepared by reaction of a compound of formula (Ia) (where R is a hydrogen atom and $R^1$ is a carboxyl protecting group) with an N-protected, carboxyl activated amino acid or peptide of formula (XIV)

$R^5O-R^7$ (XIV)

where $R^5$ is a protected amino acid or peptide as defined above and $R^7$ is any carboxyl activating group useful in conventional peptide synthesis for example a pentafluorophenyl group.

The reaction conveniently takes place in a solvent such as an amide (e.g. dimethylformamide) at a temperature in the range of $-10$ to $+30°$ C.

Subsequent elongation of the peptide chain $R^5$ may be effected by further N-deprotection and coupling steps with compounds of formula (XIV) using methods of conventional peptide synthesis.

Deprotection of amino groups may be effected using the methods described in process (B) hereinbefore.

Alternatively the compounds of formula (XI) may be prepared by methods of conventional solid phase peptide synthesis, for example those methods described in "Solid Phase Peptide Synthesis" by J. M. Stewart and J. D. Young (Pierce Chemical Co., Rockford Ill. 1984).

Thus, compounds of formula (XI) where $R^5$ is an optionally protected peptide chain and $R^6$ represents an amino acid amide residue as defined previously may be prepared by cleavage of a compound of formula (XV)

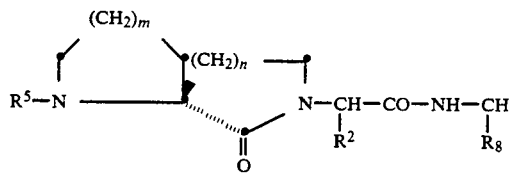

where $R^5$ is an optionally protected peptide chain, $R^8$ represents a methionyl, phenylalanyl or tryptophyl side chain or $R^8$ represents a

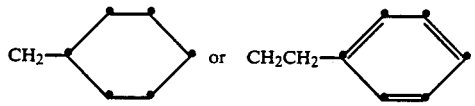

group, Nle represents norleucine and P is an aminofunctionalised polymeric solid support useful in solid phase synthesis.

Cleavage may be effected using for example liquid ammonia, or a solution of ammonia in methanol.

Compounds of formula (XV) where $R^5$ is an optionally protected peptide chain may be prepared from compounds of formula (XV) where $R^5$ is hydrogen by the sequential coupling of carboxyl activated N-protected amino acids of formula (XIV) and deprotection cycles of conventional solid phase synthesis (for example as described by Atherton et. al., J. C. S. Perkin I, p. 538, 1981).

Compounds of formula (XV) where $R^5$ is hydrogen may be prepared by reacting compounds of formula (Ia) where R is a protecting group (e.g. a t-butyloxycarbonyl or 9-fluorenylmethyloxycarbonyl group) and $R^1$ is a carboxyl activating group (for example a penta- fluorophenyl group) with a compound of formula (XVI)

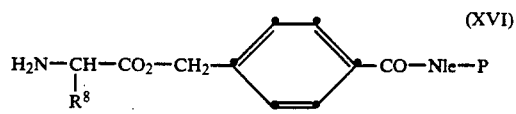

(where $R^8$, Nle and P are as defined above) followed by deprotection as described for process (B) hereinbefore.

Compounds of formula (XVI) may be prepared from a suitable polymer support such as cross-linked polystyrene or polydimethylacrylamide resin according to established methods of solid phase synthesis.

It will be appreciated that it may be necessary to protect side-chain functions of certain amino acids during the synthesis of the compounds of the invention, for example aspartic acid side chains may be protected by, for example, benzyl or t-butyl ester groups and histidine side chains may be protected by, for example, t-butyloxycarbonyl or dinitrophenyl groups.

The following Preparations and Examples are included by way of illustrating the invention. All temperatures are in ° C. 'Dried' refers to drying using magnesium sulphate or sodium sulphate. Column chromatography (CC) was carried out on silica (Merck 7734) using one of the following solvent systems: System A—chloroform:methanol:acetic acid; System B—hexane:ethyl acetate; System C—chloroform:methanol; System D—toluene:ethyl acetate; System E—diethyl ether:hexane; System F—ethyl acetate:petroleum ether (b.p. 60°–80° C.); System G—0.1% TFA in water; System H—0.1% TFA in (acetonitrile:water (9:1)). The following abbreviations are used: DCC—dicyclohexylcarbodiimide; DEA—N,N-diisopropylethylamine; DHBT —3,4-dihydro-3-hydroxy-4-oxo-1,2,3-benzotriazine; DMF—dimethylformamide; Fmoc—N-fluorenylmethoxycarbonyl; TFA—trifluoroacetic acid; THF—tetrahydrofuran. High pressure liquid chromatography (h.p.l.c) was carried out on TSK ODS-120T.

INTERMEDIATE 1

(2S)-2-propenylproline hydrochloride
3-(1,1-Dimethylethyl)-5,6,7,7a-tetrahydro-7a-(2-propenyl)-(3S-cis)-1H,3H-pyrrolo[1,2-c]oxazol-1-one (7.98 g) was dissolved in a mixture of methanol (170 ml) and water (40 ml). Silica gel (20 g) was added and the reaction was stirred for 24 h at ambient temperature. The silica was removed by filtration, washed with methanol (100 ml) and water (50 ml) and the filtrate and washes were combined, then evaporated to leave an oil which was taken up in 1M HCl (100 ml). The solution was washed with $CH_2Cl_2$ (4×50 ml) then evaporated to dryness. Residual water was removed by azeotropic evaporation with methanol to leave a brown solid (5 g) which was dried in vacuo over $P_2O_5$, leached with boiling chloroform and crystallised from methanol to give the title compound (3.68 g) m.p. 180°–183°, $[\alpha]_D+50°$ (MeOH, C=1%).

INTERMEDIATE 2

(2S)-2-(2-propenyl)-1,2-pyrrolidinedicarboxylic acid, 1-phenylmethyl ester

Intermediate 1 (3.58 g) was dissolved in a solution of sodium bicarbonate (1.56 g) in water (26 ml). Acetone (26 ml) and N-benzyloxycarbonylsuccinimide were added and the reaction was stirred for 70 h. More N-benzyloxycarbonylsuccinimide (2.5 g) was added followed by sodium bicarbonate (1.0 g). After a further 24 h the acetone was removed by evaporation and the residue was washed with dichloromethane (2×50 ml). The aqueous phase was brought to pH3 with conc. HCl solution and extracted with dichloromethane (3×50 ml). The extract was washed with water (75 ml), dried and evaporated to leave an oil (3.54 g) which was purified by CC eluting with System A (97:2:1) to give the title compound (2.25 g) as a pale yellow oil, $[\alpha]_D-6°$ (EtOAc c=1%).

INTERMEDIATE 3

2,3-Dihydro-5-hydroxy-(2'S)-2-oxospiro-[furan-3,2'-pyrrolidine]-1'-carboxylic acid phenylmethyl ester A solution of Intermediate 2 (2.75 g) in dichloromethane (30 ml) was cooled to −78° and ozone enriched oxygen was passed through the solution for 2.5 h. Dimethylsulphide (5 ml) was added then triphenylphosphine (2.48 g) and after 1 h the solvent was removed in vacuo to leave an oil (5.78 g). This was purified by CC eluting with System B (1:2) to give the title compound (1.54 g) as an oil. $\nu_{max}$ 3550, 3350, 1775, 1675.

INTERMEDIATE 4

(2R,S)-2-propenyl-1,2-pyrrolidinedicarboxylic acid 1-phenylmethyl 2-(1,1-dimethyl)ethyl diester A 2.6M solution of n-butyl lithium in hexane (385 μl) was added dropwise to a solution of hexamethyldisilazane (218 μl) in dry THF (1 ml) stirred at −30° under $N_2$. The mixture was stirred for 5 min before cooling to −70° when a solution of (2S)-1,2-pyrrolidinedicarboxylic acid, 1-phenylmethyl-2-(1,1-dimethyl)ethyl diester (305 mg) in dry THF (2 ml) was added keeping the temperature below −65°. The mixture was stirred at −70° for 0.5 h then 2-iodopropene (122 μl) was added and after a further 1h the mixture was treated with 2M HCl solution (1 ml). Diethyl ether (50 ml) and water (50 ml) were added and the aqueous phase was separated and extracted with diethyl ether (50 ml). The combined organic phase was washed with water, dried and evaporated to leave a brown oil (432 mg) which was purified by CC eluting with System D (19:1) to give the title compound (121 mg) as an oil, $(CHBr_3)\nu_{max}$ 1723, 1691, 1638, 1598, 1498, 845, 770.

INTERMEDIATE 5

(2R,S)-2-(2-oxaethyl)-1,2-pyrrolidinedicarboxylic acid, 1-phenylmethyl 2-(1,1-dimethyl)ethyl diester A solution of Intermediate 4 (9.5 g) in dichloromethane (100 ml) was cooled to −70° and ozone enriched oxygen was passed through the solution. After 0.75 h oxygen was passed through the solution to discharge the blue colouration. The solvent was removed in vacuo and the residue was redissolved in dichloromethane (100 ml). Triphenylphosphine (7 g) was added and after 1 h the mixture was evaporated to leave an oil which was purified by CC eluting with System E (1:1) to give the title compound (6.24 g) $(CHBr_3)$ $\nu_{max}$ 1750, 1680.

INTERMEDIATE 6

(2R,S)-2-[(1S)-2-[1-(methoxycarbonyl)-3-methyl-butylamino]ethyl]-1,2-pyrrolidinedicarboxylic acid 1-phenylmethyl 2-(1,1-dimethyl)ethyl diester Leucine methyl ester hydrochloride (523 mg) was treated with sodium bicarbonate (242 mg) in water (10 ml). The mixture was extracted with ethyl acetate (3×50 ml) and the extract dried and evaporated to leave an oil (275 mg). The oil was dissolved in dry THF (10 ml) and the solution added to Intermediate 5 (320 mg). 5Å molecular sieve (1.5 g) was added and the mixture was left for 2 h before adding sodium borohydride (60 mg) in methanol (3 ml). After a further 1 h the reaction mixture was decanted from the sieve which was washed with diethyl ether (2×10 ml) and the total organic phase combined, washed with water (50 ml), dried and evaporated to leave an oil (440 mg) which was purified by CC eluting with System E (1:1) to give the title compound (279 mg) as an oil, $(CHBr_3)$ $\nu_{max}$ 1730, 1692, 1599, 1498, 845, 770.

Similarly prepared:

INTERMEDIATE 7

(2R,S)-2-[(1R,S)-2-[-1-(methoxycarbonyl)-3-methyl-butylamino]ethyl]-1,2-pyrrolidinedicarboxylic acid 1-phenylmethyl 2-(1,1-dimethyl)ethyl diester (10.7 g) from Intermediate 5 (17 g,) in dry THF (200 ml), leucine methyl ester (17 g) and 4Å molecular sieve (27 g) at room temperature for 1.75 h then sodium borohydride (3 g) in methanol (60 ml).

INTERMEDIATE 8

(2R)-2-[(1S)-2-[1-(methoxycarbonyl)-3-methyl-butylamino]ethyl]-1,2-pyrrolidinedicarboxylic acid, 1-phenylmethyl ester Intermediate 6 (1.24 g) was dissolved in $TFA:H_2O$ (95:5) (40 ml) and the solution was left at room temperature for 3 h and the solvents were removed in vacuo to leave an oil. 2N hydrochloric acid solution (10 ml) and methanol (40 ml) were added and the resulting solution was evaporated to dryness. The acid treatment was repeated and the resulting oil was treated with diethyl ether (50 ml) and evaporated to dryness. Two further evaporations with ether (50 ml each) afforded the crude product as a froth (1.09 g). The mixture was purified by CC eluting with System C (19:1) to give the title compound (0.33 g), $[\alpha]_D +21°$ $(CHCl_3 c=0.82\%)$.

INTERMEDIATE 9

(2S) -2-[(1S)-2-[1-(methoxycarbonyl)-3-methyl-butylamino]ethyl]-1,2-pyrrolidinedicarboxylic acid, 1-phenylmethyl ester Further elution of the product of Intermediate 8 above afforded the title compound (0.25 g) $[\alpha]_D-20°$ $(CHCl_3 c=0.86\%)$.

Similarly prepared:

INTERMEDIATE 10

(2S)-2-[(1R)-2-[1-(methoxycarbonyl)-3-methyl-butylamino]ethyl]-1,2-pyrrolidinedicarboxylic acid 1-phenylmethyl ester and (2R)-2-[(1S)-2-[1-(methoxycarbonyl)-3-methylbutylamino]ethyl]-1,2-pyrrolidinedicarboxylic acid 1-phenylmethyl ester (2.85 g) as an enantiomeric mixture from Intermediate 7 (5.90 g);

INTERMEDIATE 11

(2S)-2-[(1S)-2-[1-(methoxycarbonyl)-3-methyl-butylamino]ethyl]-1,2-pyrrolidinedicarboxylic acid 1-phenyl-methyl ester and (2R)-2-[(1R)-2-[1-(methoxycarbonyl)-3-methylbutylamino]ethyl]-1,2-pyrrolidinedicarboxylic acid, 1-phenylmethyl ester (1.25 g) as an enantiomeric mixture from Intermediate 7 (5.90 g).

INTERMEDIATE 12

1,2-Piperidinedicarboxylic acid, 1-phenylmethyl ester

A solution of N-benzyloxycarbonyl succinimide (12.29 g) in acetone (50 ml) was added to a solution of pipecolinic acid (10.0 g) and sodium bicarbonate (6.5 g) in a mixture of water (105 ml) and acetone (50 ml). After 24 h the acetone was removed by evaporation and the residue was washed with diethyl ether (2×50 ml), then brought to pH2 with conc. HCl. The product was extracted into ethyl acetate (3×100 ml) and the extract washed with water (100 ml) and brine (100 ml), dried and evaporated to leave an oil (14.78 g). The ethereal wash was evaporated to dryness and the residue was taken up in water. After filtration the solution was brought to pH2 and extracted with ethyl acetate. The organic phase was extracted with 5% sodium bicarbonate solution (x4), the extract brought to pH2 with conc. HCL and the product extracted into ethyl acetate. The extract was washed with water and brine, dried and evaporated to leave an oil (3.28 g). The two product fractions were combined and purified by CC eluting with System A (98:1:1) to give the title compound (11.34 g) as a pale yellow oil, NMR (CDCl$_3$) $\delta$1.25-2.4(6Hm), 3.0(1Hm), 4.1(1Ht), 5.05(1Hm), 5.15(2Hq), 7.35(5Hm), 9.75(1Hm).

INTERMEDIATE 13

1,2-Piperidinedicarboxylic acid 1-phenylmethyl 2-(1,1-dimethyl)ethyl diester

Intermediate 12 (0.53 g), 4-dimethylaminopyridine (0.24 g) and t-butanol (0.18 g) were dissolved in dichloromethane (3 ml) and cooled in ice. Dicyclohexylcarbodiimide (0.45 g) in dichloromethane (3 ml) was added. The mixture was warmed to room temperature and left for 18 h, then filtered. The filter pad was washed with dichloromethane (10 ml) and the combined organic phase was evaporated to leave an oily solid. Ethyl acetate (20 ml) was added and the mixture was washed with 10% citric acid solution (3×10 ml), water (2×10 ml) and brine (20 ml) then dried and evaporated. The residue was taken up in System B (9:1) (95 ml) and the solution filtered and evaporated to leave an oil (0.62 g) which was purified by CC eluting with System B (9:1) to give the title compound (0.50 g) as an oil, NMR (CDCl$_3$) $\delta$1.4 and 1.43 (9 Hs), 1.25(2 Hm), 1.65(3 Hm), 2.2(1 Hm), 3.05(1 Hm), 4.05(1 Hm), 4.75(1 Hm), 5.05 and 5.2 and 5.15 (2H ABq) 7.35 (5 Hm).

INTERMEDIATE 14

(2R,S)-2-(2-Propenyl)-1,2-piperidinedicarboxylic acid, 1-phenylmethyl 2-(1,1-dimethyl)ethyl diester A 2.4M solution of n-butyllithium in hexane (2.08 ml) was added to a solution of hexamethyldisilazane (1.09 ml) in dry THF (5 ml) stirred at $-35°$ under N$_2$ over 3 min. The mixture was stirred for 5 min. at $-35°$ before cooling to $-70°$. A solution of Intermediate 13 (1.6 g) in THF (5 ml) was added keeping the temperature below $-65°$. The mixture was stirred at $-70°$ for 0.5 h the 2-iodopropene (0.61 ml) was added. The reaction was stirred at $-70°$ for 1 h, then at $-40°$ for a further 2 h then gradually warmed over 1 h to 0°. 2M HCl (5 ml) was added and the mixture brought to room temperature before adding diethyl ether (50 ml) and water (100 ml). The aqueous phase was extracted with ether (2×50 ml) and the combined ethereal phase washed with water (100 ml), dried and evaporated to leave a pale yellow oil (1.68 g) which was purified by CC eluting with System B (1:1) to give the title compound (1.07 g) as an oil which crystallised on standing mp. 60°-62°.

INTERMEDIATE 15

(2R,S)-2-(2-oxaethyl)-1,2-piperidinedicarboxylic acid, 1-phenylmethyl 2-(1,1-dimethyl)ethyl diester A solution of Intermediate 14 (1.0 g) in dichloromethane (14 ml) was cooled to $-78°$ and ozone enriched oxygen passed through the solution until a blue colouration appeared after 20 min. After a further 10 min oxygen was passed through the solution to discharge the colour. The mixture was evaporated to leave an oil (1.35 g) which was dissolved in dichloromethane (10 ml) and triphenylphosphine (0.73 g) was added. After a further 1 h the solvent was removed by evaporation and the residue purified by CC eluting with System E to give the title compound (0.4 g) as an oil which crystallised on standing mp. 54°-57°.

INTERMEDIATE 16

2-[(1S)-2-[1-(methoxycarbonyl)-3-methylbutylamino]ethyl]-(2R,S)-1,2-piperidinedicarboxylic acid, 1-phenylmethyl 2-(1,1-dimethyl)ethyl diester Leucine methyl ester hydrochloride (0.95 g) was partitioned between 5% NaHCO$_3$ solution (50 ml) and ethyl acetate (50 ml). The aqueous phase was extracted with ethyl acetate (5×40 ml), and the combined organic phase was dried and evaporated to give a mobile oil (0.62 g) which was dissolved in dry THF (20 ml). The solution was added to the aldehyde Intermediate 15 (0.63) and 4 Å molecular sieve (1.0 g) added. After 2 h a mixture of sodium borohydride (0.12) and methanol (6 ml) was added and the reaction was left for 4 h before filtering to removed the sieves which were washed with THF (20 ml). The combined organic phase was concentrated by evaporation, diluted with diethyl ether (50 ml) and water (50 ml). The organic phase was washed with water (2×50 ml), dried and separated to leave an oil (0.83 g) which was purified by CC eluting with System B (3:2) to give the title compound (0.56 g) $[\alpha]_D - 15.0°$ (EtOAc, c=1%).

INTERMEDIATE 17

2-[(1S)-2-[1-(methoxycarbonyl)-3-methylbutylamino]ethyl]-(2R)-1,2-piperidinedicarboxylic acid, 1-phenylmethyl ester A solution of Intermediate 16 (2.6 g) in TFA: H$_2$O (95:5, 60 ml) at 0° was allowed to warm to room temperature and left for 4 h. The solvent was removed by evaporation and the residue treated with 2M aqueous HCl in methanol. The solvents were removed by evaporation and the residue dissolved in methanol (40 ml) and the solution evaporated to dryness to leave an oil which was again dissolved in methanol evaporated to leave an oil (3.22 g) which was purified by extensive CC eluting with System C (9:1) to give the title compound (0.51 g) $[\alpha]_D 15°$ (EtOAc c=1%).

INTERMEDIATE 18

2-[(1S)-2-[1-(methoxycarbonyl)-3-methylbutylamino]ethyl]-(2S)-1,2-piperidinedicarboxylic acid 1-phenylmethyl ester Further elution of Intermediate 17 afforded the title compound (0.60 g) $[\alpha]_D -46°$ (EtOAc c=1%).

INTERMEDIATE 19

$N^1$-[N-[(1,1-dimethylethoxy)carbonyl]-L-phenylalanyl]-4-methyl-2S-(6-oxo-5S-1,7-diazaspiro[4.4]nonan-7-yl)-pentanoic acid methyl ester A solution of the product in Example 6 (51 mg) and t-butoxycarbonylphenylalanine pentafluorophenyl ester (160 mg) in DMF (1.7 ml) was cooled in ice and triethylamine (28 μl) was added. The mixture was warmed to room temperature and left for 48 h. The reaction was cooled in ice and 4-(2-aminoethyl)-morpholine (25 μl) was added. After 0.5 h at 0° C. the reaction was diluted with ethyl acetate (60 ml) and washed with citric acid solution (3×20 ml), 10% sodium carbonate solution (3×20 ml), water (20 ml) and dried and evaporated to leave an oil which was purified by CC eluting with System F (1:1) to give the title compound as an oil, NMR (CDCl₃) δ0.8–1.0(6 Hm), 1.7–1.5(1 Hm), 1.4(9 Hs), 1.6–2.0(7 Hm), 2.7(1 Hm), 2.75(1 Hm), 2.95 and 3.06 (2 Hm), 3.15(1 Hm), 3.44(1 Hm), 3.67(1 Ht), 3.75(3 Hs), 4.58(1 Hm), 4.85(1 Hm), 5.52(1 Hd), 7.25(5 Hm).

Similarly prepared:

INTERMEDIATE 20

$N^1$-[N-[(1,1-dimethylethoxy)carbonyl]-L-phenylalanyl]-4-methyl-2R-(6-oxo-5R-1,7-diazasprio[4.4]nonan-7-yl)-pentanoic acid methyl ester (327 mg) from the product of Example 5 (1.69 g), NMR (CDCl₃) δ0.9–1.0(6 Hm), 1.34(9 Hs), 1.44(1 Hm), 1.6–2.1 (7 Hm), 2.7 (1 Hm), 2.83(1 Hdd), 3.14(1 Hdd), 3.18–3.35(2 Hm), 3.75(3 Hs), 3.65–3.85 (2 Hm), 4.62(1 Hm), 4.85(1 Hdd), 5.3(1 Hd), 7.23(5 Hm).

INTERMEDIATE 21

$N^1$-[N-[(1,1-dimethylethoxy)carbonyl]-L-phenylalanyl]-4-methyl-2R-(6-oxo-5S-1,7-diazaspiro[4.4]nonan-7-yl) pentanoic acid, methyl ester (55 mg) from the product of Example 4 (250 mg).

NMR (CDCl₃) δ0.95–1.05(6 Hm), 1.44(9 Hs), 1.49(1 Hm), 1.65–2.2(7 Hm), 2.64(1 Hm), 2.76(1 Hm), 2.93(1 Hdd), 3.1(1 Hdd), 3.3–3.6(3 Hm), 3.69(3 Hs), 4.58(1 Hm), 4.86(1 Hm), 5.44(1 Hd), 7.25(5 Hm), and

INTERMEDIATE 22

$N^1$-[N-[(1,1-dimethylethoxy)carbonyl]-L-phenylalanyl]-4-methyl-2S-(6-oxo-5R-1,7-diazaspiro[4.4]nonan-7-yl)-pentanoic acid methyl ester (33 mg) from the product of Example 4 (250 mg).

NMR (CDCl₃) δ0.95–1.05 (6 Hm), 1.38(9 Hs), ~1.4(1 Hm), 1.7–2.15(7 Hm), 2.63 (1 Hm), 2.86, (1 Hdd), 3.08 (1 Hdd), 3.12(1 Hm), 3.3–3.5(2 Hm), ~3.65(1 Hm), 3.71(3 Hs), 4.6(1 Hm), 4.94(1 Hm), 5.25(1 Hd), 7.15–7.35(5 Hm)

INTERMEDIATE 23

$N^1$[N-[(1,1-dimethylethoxy)carbonyl]-L-phenylalanyl-L-phenylalanyl]-4-methyl-2S-(6-oxo-5S-1,7-diazaspiro[4.4]nonan-7-yl)-pentanoic acid methyl ester Intermediate 19 (142 mg) was dissolved in 4M HCl in dioxan (5 ml) and after 0.5 h the solvent was removed by evaporation to leave an oil which was dissolved in diethyl ether (10 ml) then evaporated to dryness. The residue was dissolved in dichloromethane (5 ml) and diluted with hexane (50 ml) to produce an oil. The solvents were decanted off and the oil dried in vacuo. Ether was added and the liquid evaporated to give a solid (84 mg). The solid was added to a solution of t-butoxycarbonylphenylalanine pentafluorophenyl ester (160 mg) in DMF (1.7 ml) cooled in ice then triethylamine (28 μl) was added and the mixture was kept at 0° C. for 2 h. 4-(2-Aminoethyl) morpholine (25 μl) was added and after 25 min the mixture was diluted with ethyl acetate (30 ml), washed with 10% citric acid solution (3×20 ml), water (2×20 ml) and 5% sodium bicarbonate solution (2×20 ml), dried and evaporated to leave an oil which was purified by CC eluting with System B (1:1) then ethyl acetate to give the title compound (119 mg).

INTERMEDIATE 24

$N^1$-[N-[N-[(1,1-dimethylethoxy)carbonyl]-5-aminopentanoyl]-L-phenylalanyl-L-phenylalanyl]-4-methyl-2S-(6-oxo-5S-1,7-diazaspiro[4.4]nonan-7-yl)-pentanoic acid, methyl ester Intermediate 23 (114 mg) was dissolved in 4 MHCl in dioxan (5 ml) and after 0.5 h the solvent was removed by evaporation to leave an oil which was dried in vacuo then dissolved in diethyl ether (10 ml). The solution was evaporated to leave a solid which was dried in vacuo (102 mg). The solid was dissolved in DMF (1.5 ml) and t-butoxycarbonyl-5-aminopentanoic acid pentafluorophenyl ester (130 mg) was added to the ice cold solution. Triethylamine (28 μl) was added and the mixture kept at ice temperature for 2 h before adding 4-(2-aminoethyl)-morpholine (25 μl). After a further 0.5 h the mixture was diluted with ethyl acetate (40 ml), washed with 10% citric acid solution (3×20 ml), water (20 ml) and 5% sodium bicarbonate solution (2×20 ml), dried and evaporated to leave an oil which was purified by CC eluting with ethyl acetate to give the title compound (110 mg) as a froth.

INTERMEDIATE 25

$N^1$-[N-[N-[(1,1-dimethylethoxy)carbonyl]-5-amino-pentanoyl]-L-phenylalanyl-L-phenylalanyl]-4-methyl-2S-(6-oxo-5S-1,7-dia-zaspiro[4.4]nonan-7-yl)pentoic acid 1M sodium hydroxide (289 μl) was added to ice-cold solution of Intermediate 24 (110 mg) in methanol (1.3 ml). After 0.5 h the reaction was warmed to room temperature and left for a further 6.5 h. Acidification with 10% citric acid solution (1 ml) and dilution with water (20 ml) gave an oil that was extracted into ethyl acetate (3×20 ml). The extract was dried and evaporated to leave the title compound (106 mg) as an oil.

EXAMPLE 1

7-[(1S)-(1-methoxycarbonyl)-3-methylbutyl]-6-oxo-(5S)-1,7-diazaspiro[4.4]nonane-1-carboxylic acid, phenylmethyl ester Sodium cyanoborohydride (0.32 g) was added to a solution of Intermediate 3 (1.47) and leucine methyl ester (0.77) in methanol (10 ml) and the reaction was stirred at room temperature for 28 h. The methanol was removed in vacuo and the residue purified by CC eluting with System C (9:1) to give a solid which was dissolved in chloroform (100 ml) and left at room temperature for 72 h. The solution was washed with 10% citric acid solution (×2), 10% $Na_2CO_3$ solution (×2) and water (×1), dried and evaporated to leave an oil which was crystallised from diethyl ether to give the title compound (0.54) m.p. 110°-112°, [α]$_D$−12° (CHCl$_3$ c=1%).

EXAMPLE 2

7-[(1S)-(1-methoxycarbonyl)-3-methylbutyl]-6-oxo-(5R)-1,7-diazaspiro[4.4]nonane-1-carboxylic acid phenylmethyl ester Intermediate 8 (290 mg) was dissolved in dichloromethane (10 ml) and added to DCC (142 mg) in dichloromethane (5 ml). After 3 h the mixture was filtered and the filter pad washed with dichloromethane (10 ml). The filtrate and wash were combined and evaporated to leave an oil which was purified by CC eluting with System B (1:2). The resultant product (323 mg) was dissolved in diethyl ether (20 ml) and cooled to 5° and filtered. The filtrate was evaporated to leave an oil which was further purified by CC eluting with System D (2:1) to give the title compound (0.27 g) [α]$_D$−37° (CHCl$_3$ c=1%) NMR (CDCl$_3$) δ0.83 and 0.98 (6 Hm), 1.3 (1 Hm), 1.5–2.3 (7 Hm), 2.45 and 2.66 (1 Hm), 3.3 (1 Hm), 3.4(1 Hm), 3.63(2 Hm), 3.7 and 3.72 (3H s), 4.82 and 4.92 (1 Hm), 4.84 and 5.38 and 5.08 and 5.15 (2 Hm), 7.35 (5 Hm).

EXAMPLE 3

7-[(1S)-(1-methoxycarbonyl)-3-methylbutyl]-6-oxo-(5S)-1,7-diazaspiro[4.4]nonane-1-carboxylic acid phenylmethyl ester A solution of Intermediate 9 (210 mg) in dichloromethane (10 ml) was treated with 1-ethyl-3-(3-dimethylaminopropyl) carbodiimide hydrochloride (97 mg). After 3 h the reaction was diluted with diethyl ether (50 ml) and washed with water (2×20 ml), dried and evaporated to leave an oil which crystallised on the addition of diethyl ether (5 ml). The ether was removed in vacuo and the solid dried in vacuo (199 mg). The solid was recrystallised from diethyl ether to give the title compound (131 mg) m.p. 111°-113° C., [α]$_D$−8° (CHCl$_3$ c=1%).

Similarly prepared:

EXAMPLE 4

7-[(1S)-(1-methoxycarbonyl)-3-methylbutyl]-6-oxo-(5R)-1,7-diazaspiro[4.4]nonane-1-carboxylic acid, 1-phenylmethyl ester and 7-[(1R)-(1-methoxycarbonyl)-3-methylbutyl]-6-oxo-(5S)-1,7-diazaspiro[4.4]nonane-1-carboxylic acid, 1-phenylmethyl ester (3.5 g) as an enantiomeric mixture from Intermediate 10 (3.75 g).

EXAMPLE 5

7-[(1S)-(1-methoxycarbonyl)-3-methylbutyl]-6-oxo-(5S)-1,7-diazaspiro[4.4]nonane-1-carboxylic acid, 1-phenylmethyl ester and 7-[(1R)-(1-methoxycarbonyl)-3-methylbutyl]-6-oxo-(5R)-1,7-diazaspiro[4.4]nonane-1-carboxylic acid, 1-phenylmethyl ester (1.10 g), m.p. 105°-107°, as an enantiomeric mixture from Intermediate 11 (1.25 g).

EXAMPLE 6

4-methyl-2-(2S)-[(5S)-6-oxo-1,7-diazaspiro[4.4]nonan-7-yl]-pentanoic acid methyl ester A solution of the protected spiro derivative, Example 1, (2.17 g) in methanol (150 ml) containing HCl (from 1.2 ml acetyl chloride) was hydrogenated over 10% Pd-C catalyst (0.35 g) for 3 h. The catalyst was removed by filtration, the filtrate was concentrated, diluted with diethyl ether and evaporated to dryness. The sticky solid (1.62 g) was recrystallised from ethyl acetate to give the title compound (0.73 g) m.p. 186°-189°, [α]$_D$−14° (CHCl$_3$ c=1%).

EXAMPLE 7

7-[(1S)-(1-methoxycarbonyl)-3-methylbutyl]-6-oxo-(5S)-1,7-diazaspiro[4.4]nonane-1-carboxylic acid, (1,1-dimethyl)ethyl ester A solution of the amine, Example 6 (720 mg) in dioxan (20 ml) was stirred with NaHCO$_3$ (500 mg) in water (50 ml). Di-t-butyl pyrocarbonate (1.1 g) in dioxan (30 ml) was added and after 24 h the mixture was diluted with water (200 ml) and extracted with diethyl ether (3×50 ml). The extract was dried and evaporated to leave an oil which was purified by CC eluting with System B (1:1) and crystallised from hexane to give the title compound (748 mg) m.p. 87°–88°, NMR (CDCl$_3$) δ0.9–1.0 (6 Hm), 1.35 (1 Hm). 1.39 and 1.44 (9 Hs), 1.5–2.1 (7H m), 2.53 and 2.7 (1 Hm), 3.14 (1 Hm), 3.45–3.65 (3 Hm), 3.68 and 3.74 (3 Hs), 4.84 and 4.94 (1 Hm).

EXAMPLE 8

7-[(1S)-(1-carboxy)-3-methylbutyl]-6-oxo-(5S)-1,7-diazaspiro[4.4]nonane-1-carboxylic acid (1,1-dimethyl)ethyl ester A solution of the methyl ester, Example 7 (709 mg) in methanol (10 ml) was cooled in ice and 1M NaOH solution (3.85 ml) was added. After 0.5 h the mixture was warmed to RT and left for 2.5 h. The reaction was brought to pH3 with 10% citric acid solution, diluted with water (10 ml) and extracted with diethyl ether (2×50 ml). The extract was dried and evaporated to leave a froth (692 mg) which was crystallised from diethyl ether to give the title compound (462 mg) mp. 187°-189°, [α]$_D$−47° (CHCl$_3$ c=1%).

EXAMPLE 9

4-methyl-2S-[1-8 (fluoren-9-yl)methoxycarbonyl]-6-oxo-5S-1,7-diazaspiro[4.4]nonan-7-yl]-pentanoic acid 1M Sodium hydroxide solution (3 ml) was added to an ice-cold solution of Example 6 (305 mg) in methanol (10 ml). The mixture was kept at 5° for 18 h then neutralised with 2M HCl solution (1 ml). The mixture was evaporated to low bulk then sodium carbonate (212 mg) was added followed by a solution of fluorenylmethoxycarbonyl succinimide (353 mg) in acetone (10 ml). Water (7 ml) was added and the mixture was left at room temperature for 2.5 h, then brought to pH3 with 10% citric acid solution and diluted with water. The product was extracted into dichloromethane (3×70 ml) and the extract evaporated to leave a solid (484 mg) which was stirred with ethyl acetate (50 ml) for 1 h then collected by filtration, washed with ethyl acetate and dried to give the title compound (341 mg) mp. 197°-198°, [α]$_D$−40° (CHCl$_3$ c=1%).

EXAMPLE 10

4-methyl-2S-[1-[(fluoren-9-yl)methoxycarbonyl]-6-oxo-5S-1,7-diazasiro[4.4]nonan-7-yl]-pentanoic acid, pentafluorophenyl ester A partial suspension of Example 9 (565 mg) in dioxan (20 ml) was stirred for 3 h at room temperature with pentafluorophenol (218 mg) and DCC (245 mg) and left at 5° for 72 h. The mixture was filtered and the pad washed with ethyl acetate (20 ml). The combined organic phase was evaporated to leave a solid which was dried in vacuo, dissolved in ethyl acetate and refrigerated. The mixture was filtered and the filtrate diluted with three volumes of hexane to give the title compound (647 mg) as a solid, mp. 176°–177°, $[\alpha]_D -24°$ (CHCl$_3$ c=1%).

EXAMPLE 11

8-[(1S)-(1-methoxycarbonyl)-3-methylbutyl]-7-oxo-(6R)-1,8-diazaspiro[5.4]decane-1-carboxylic acid 1-phenylmethyl ester A solution of Intermediate 18 (0.52 g) in dichloromethane (50 ml) was treated with 1-ethyl-3-(3-dimethylaminopropyl) carbodiimide hydrochloride (250 mg). After 3 h the solvent was removed by evaporation and the residue dissolved in ethyl acetate (25 ml). The solution was washed with 10% citric acid solution (3×25 ml), water (2×25 ml) and brine (30 ml), dried and evaporated to leave the title compound (0.46 g) as an oil which crystallised on standing mp. 71°–73° C., $[\alpha]_D -40°$ (MeOH c=1.0%).

EXAMPLE 12

8-[(1S)-(1-methoxycarbonyl)-3-methylbutyl]-7-oxo-(6S)-1,8-diazaspiro[5.4]decane-1-carboxylic acid 1-phenylmethyl ester The amino acid Intermediate 16 (0.55 g) was dissovled in dichloromethane (50 ml) and 1-ethyl-3-(3-dimethylaminopropyl) carbodiimide hydrochloride (0.27 g) was added. After 3.5 h the solution was washed with 10% citric acid solution (2×25 ml), water (2×25 ml) and dried. Evaporation gave an oil which crystallised on the addition of diethyl ether. The ether was removed to give the title compound (0.35 g) as a solid mp. 99°–100° C., $[\alpha]_D -8°$ (MeOH c=1%).

EXAMPLE 13

4-methyl 2-(2S)-[(6S)-7-oxo-1,8-diazaspiro[5.4]decan-8-yl]-pentanoic acid, methyl ester A solution of the spiro derivative Example 12 (0.21 g) in methanol (60 ml) containing HCl (from 150 μl acetyl chloride) was hydrogenated over 10% Pd-C (150 mg) for 2 h. The catalyst was removed by filtration and washed with methanol (30 ml). The combined organic phase was evaporated to dryness and the residue dissolved in ethyl acetate (60 ml) and methanol (6 ml) and filtered. The filtrate was evaporated to leave the title compound (0.15 g) as a solid mp. 165°–168° C., $[\alpha]_D -36°$ (MeOH c=1%).

EXAMPLE 14

N-[N$^1$-[N-(5-aminopentanoyl)-L-phenylalanyl-L-phenylalanyl]-4-methyl-1-oxo-2S-(6-oxo-5S-1,7-diazaspiro[4.4]nonan-7-yl)-pentyl]-L-tryptophanamide The product of Intermediate 25 (70 mg) and L-tryptophanamide hydrochloride (27 mg) were dissolved in DMF (1 ml) and cooled in ice. 1-hydroxybenzotriazole (13 mg), triethylamine (13 μl) and DCC (20 mg) were added. After 5 days more DCC (20 mg), 1-hydroxybenzotriazole (13 mg), tryptophanamide hydrochloride (27 mg) and triethylamine (13 μl) were added. After a further 3 days the reaction was diluted with ethyl acetate (15 ml), filtered and washed with 10% citric acid solution (×3), 10% sodium carbonate solution (×3), water and brine, dried and evaporated to leave a froth (81 mg). The froth was dissolved in 1.5M HCl in acetic acid and the solution was left for 1 h. The solvents were removed by evaporation in vacuo to give a white solid (82 mg) which was purified by preparative h.p.l.c. using gradient elution of systems G and H to give the title compound (65 mg). 99% pure by h.p.l.c. MH+ 833.

Similarly prepared:

EXAMPLE 15

N-[N$^1$-[N-(5-aminopentanoyl)-L-phenylalanyl-L-phenylalanyl]-4-methyl-1-oxo-2S-(6-oxo-5S-1,7-diazaspiro[4.4]nonan-7-yl]pentyl]-L-methionamide, MH+ 778, 99% pure by h.p.l.c.

EXAMPLE 16

N-[N$^1$-[N-(5-aminopentanoyl)-L-phenylalanyl-L-phenylalanyl]-4-methyl-1-oxo-2R-(6-oxo-5S-1,7-diazaspiro[4.4]nonan-7-yl)pentyl]-L-methionamide, MH+ 778, 100% pure by h.p.l.c.

EXAMPLE 17

N-[N$^1$-[N-(5-aminopentanoyl)-L-phenylalanyl-L-phenylalanyl]-4-methyl-1-oxo-2S-(6-oxo-5S-1,7-diazaspiro[4.4]nonan-7-yl)pentyl]-D-methionamide, MH+ 778, 99% pure by h.p.l.c.

EXAMPLE 18

N-[N$^1$-[N-(5-aminopentanoyl)-L-phenylalanyl-L-phenylalanyl]-4-methyl-1-oxo-2S-(6-oxo-5S-1,7-diazaspiro[4.4]nonan-7-yl)pentyl]-L-phenylalanamide, MH+ 794, 97.6% pure by h.p.l.c.

EXAMPLE 19

N-[N$^1$-[N-(5-aminopentanoyl)-L-phenylalanyl-L-phenylalanyl]-4-methyl-1-oxo-2S-(6-oxo-5S-1,7-diazaspiro[4.4]nonan-7-yl)pentyl]-L-homophenylalanamide, MH+ 808, 100% pure by h.p.l.c.

EXAMPLE 20

N-[N$^1$-[N-(5-aminopentanoyl)-L-phenylalanyl-L-phenylalanyl]-4-methyl-1-oxo-2S-(6-oxo-5S-1,7-diazaspiro[4.4]nonan-7-yl)pentyl]-L-cyclohexylalanamide, MH+ 800, 99.8% pure by h.p.l.c.

EXAMPLE 21

N-[N$^1$-[N-(5-aminopentanoyl)-L-phenylalanyl-L-phenylalanyl]-4-methyl-1-oxo-2S-(6-oxo-5S-1,7-diazaspiro[4.4]nonan-7-yl)pentyl)-2S-2-amino-4-methylpentan-1-ol, MH+ 747, 95.5% pure by h.p.l.c.

EXAMPLE 22

N-[N$^1$-[pyroglutamyl-L-phenylalanyl-L-phenylalanyl]-4-methyl-1-oxo-2S-(6-oxo-5S-1,7-diazaspiro[4.4]nonan-7-yl)pentyl]-L-methionamide, MH+ 790, 99% pure by h.p.l.c.

EXAMPLE 23

N-[N$^1$-[N-(5-aminopentanoyl)-L-phenylalanyl-L-phenylalanyl]4-methyl-1-oxo-2S-(7-oxo-6S-1,8-diazaspiro[5.4]decan-8-yl)pentyl]-L-methionamide, MH+ 792, 100% pure by h.p.l.c.

EXAMPLE 24

N-[N$^1$-[N-(5-aminopentanoyl)-L-phenylalanyl-L-phenylalanyl]-4-methyl-1-oxo-2S-(6-oxo-5R-1,7-diazaspiro[4.4]nonan-7-yl]pentyl]-L-methionamide, MH+ 778, 98% pure by h.p.l.c.

EXAMPLE 25

N-[N$^1$-[L-Arginyl-L-prolyl-L-lysyl-L-prolyl-L-glutaminyl-L-glutaminyl-L-phenylalanyl-L- phenylalanyl]-4-methyl-1-oxo-2S-(6-oxo-5S-1,7-diazaspiro[4.4]nonan-7-yl)-pentyl]-L-tryptophanamide.

Kieselguhr supported polydimethylacrylamide resin (0.09 mmol/g loading, 1.5 g) was treated with ethylenediamine for 18 h at room temperature in a continuous flow synthesiser. The resin was washed with DMF, 10% DEA in DMF then DMF and the resulting resin-bound amine was acylated with Fmoc-norleucine pentafluorophenyl ester (0.14 g) in the presence of DHBT (0.04 g) in DMF over 50 min. The resin was washed with DMF, the resin-bound norleucine deprotected with 20% piperidine in DMF and the resin was again washed with DMF. p-Hydroxymethyl benzoic acid pentafluorophenyl ester (0.09 g) and DHBT (0.041 g) in DMF were reacted with the resin-bound norleucine over 18 h followed by a resin wash with DMF, 10% DEA in DMF and finally DMF. The functionalised resin was acylated with Fmoc-tryptophan symmetrical anhydride (0.23 g) in DMF using 4-dimethylaminopyridine (0.032 g) as catalyst over 50 min. This acylation was repeated using fresh reagents for a further 50 min then the resin was washed with DMF. After deprotection with 20% piperidine in DMF and a DMF wash, the resin-bound tryptophan was acylated in DMF with the product from Example 10 (0.17 g) for 50 min. The resin was washed with DMF and the usual deprotection/wash sequence was performed, followed by acylation with Fmoc-phenylalanine symmetrical anhydride (0.21 g) in DMF for 50 min then finally a DMF wash. The resin-bound peptide was deprotected and washed, then reacted with Fmoc-phenylalanine pentafluorophenyl ester (0.15 g) and DHBT (0.04 g) in DMF and finally washed with DMF. This cycle was repeated using the following Fmoc-amino acid pentafluorophenyl esters for acylations: glycine (0.14 g), glycine (0.144 g), proline (0.14 g), lysine (Boc) (0.17 g) and proline (0.14 g). The resin-bound peptide was deprotected, washed with DMF then reacted with $N^\alpha$-t-butoxycarbonylarginine hydrochloride symmetrical anhydride (0.34 g) for 25 mins in DMF. The acylation was repeated using fresh reagents for a further 25 min, the resin washed with DMF and a final acylation with fresh reagents for 1 h performed. The resin was washed with DMF, shrunk with diethyl ether and dried in vacuo to give the fully functionalised resin (1.74 g). The peptide was cleaved from the resin over 18 h with liquid ammonia in the presence of acetic acid (120 μl) using a pressure vessel charged to 7 bar. Methanol (30 ml) was added to the cooled (−70° C.) mixture and the resin was removed by filtration and washed with methanol (20 ml). The combined organic phase was evaporated to leave a solid (0.374 g) which was dissolved in 1.5M HCl in acetic acid. After 1 h the solvent was removed by evaporation, the residue taken up in water (5 ml), and the solution was freeze-dried. The solid (0.26 g) was purified by preparative h.p.l.c. by gradient elution using Systems G and H to give the title compound (0.13 g). MH+ 1468, 99% pure peptide by h.p.l.c.

Similarly prepared:

EXAMPLE 26

N-[$N^1$-[L-prolyl-L-glutaminyl-L-glutaminyl-L-phenylalanyl-L-phenylalanyl]-4-methyl-1-oxo-2S-(6-oxo-5S-1,7-diazaspiro[4.4]nonan-7-yl)pentyl]-L-methionamide, MH+ 1032, 99% pure by h.p.l.c.

EXAMPLE 27

N-[$N^1$[L-arginyl-L-prolyl-L-lysyl-L-prolyl-L-glutaminyl-L-glutaminyl-L-phenylalanyl-L-phenylalanyl]-4-methyl-1-oxo-2S-(6-oxo-5S-1,7-diazaspiro[4.4]nonan-7-yl)pentyl]-L-methionamide, MH+ 1413, 97% pure by h.p.l.c.

EXAMPLE 28

N-[$N^1$-[L-pyroglutamyl-L-prolyl-L-aspartyl-L-prolyl-L-asparagyl-L-alanyl-L-phenylalanyl-L-tyrosyl]-4-methyl-1-oxo-2S-(6-oxo-5S-1,7-diazaspiro[4.4]nonan-7-yl)pentyl]-L-tryptophanamide, MH+ 1355, 99% pure by h.p.l.c.

EXAMPLE 29

N-[$N^1$-[L-pyroglutamyl-L-prolyl-L-aspartyl-L-prolyl-L-glutaminyl-L-glutaminyl-L-phenylalanyl-L-phenylalanyl]-4-methyl-1-oxo-2S-(6-oxo-5S-1,7-diazaspiro[4.4]nonan-7-yl)pentyl]-L-tryptophanamide, MH+ 1410, 100% pure by h.p.l.c.

EXAMPLE 30

N-[$N^1$-[L-pyroglutamyl-L-alanyl-L-aspartyl-L-prolyl-L-asparaginyl-L-lysyl-L-phenylalanyl-L-tyrosyl]-4-methyl-1-oxo-2S-(6-oxo-5S-1,7-diazaspiro[4.4]nonan-7-yl)pentyl]-L-trytophanamide, MH$^4$ 1386, 99% pure by h.p.l.c.

EXAMPLE 31

N-[$N^1$-[L-pyroglutamyl-L-alanyl-L-asparaginyl-L-prolyl-L-asparaginyl-L-lysyl-L-phenylalanyl-L-tyrosyl]-4-methyl-1-oxo-2S-(6-oxo-5S-1,7-diazaspiro[4.4]nonan-7-yl)pentyl]-L-tryptophanamide, MH+ 1385, 1 peak by h.p.l.c.

EXAMPLE 32

N-[$N^1$-[L-pyroglutamyl-L-prolyl-L-aspartyl-L-prolyl-L-asparaginyl-L-lysyl-L-phenylalanyl-L-tyrosyl]-4-methyl-1-oxo-2S-(6-oxo-5S-1,7-diazaspiro[4.4]nonan-7-yl)pentyl]-L-tryptophanamide, MH+ 1412, 97% pure by h.p.l.c.

EXAMPLE 33

N-[$N^1$-[L-pyroglutamyl-L-alanyl-L-aspartyl-L-prolyl-L-asparaginyl-L-glutaminyl-L-phenylalanyl-L-tyrosyl]-4-methyl-1-oxo-2S-(6-oxo-5S-1,7-diazaspiro[4.4]nonan-7-yl)pentyl]-L-tryptophanamide, MH+ 1386, 99% pure by h.p.l.c.

EXAMPLE 34

N-[$N^1$-[L-pyroglutamyl-L-alanyl-L-aspartyl-L-prolyl-L-asparaginyl-L-methionyl-L-phenylalanyl-L-tyrosyl]-4-methyl-1-oxo-2S-(6-oxo-5S-1,7-diazaspiro[4.4]nonan-7-yl)pentyl]-L-tryptophanamide, MH+ 1388, 96% pure by h.p.l.c.

EXAMPLE 35

N-[$N^1$-[L-phenylalanyl-L-phenylalanyl]-4-methyl-1-oxo-2S-(6-oxo-5S-1,7-diazaspiro[4.4]nonan-7-yl)pentyl]-L-tryptophanamide, MH+ 734, 87% pure by h.p.l.c.

EXAMPLE 36

N-[$N^1$-[L-glutaminyl-L-glutaminyl-L-phenylalanyl-L-Phenylalanyl]-4-methyl-1-oxo-2S-(6-oxo-5S-1,7-diazaspiro[4.4]nonan-7-yl)pentyl]-L-tryptophanamide, MH+ 991, 78% pure by h.p.l.c.

EXAMPLE 37

N-[N$^1$-[L-lysyl-L-prolyl-L-glutaminyl-L-glutaminyl-L-phenylalanyl-L-phenylalanyl]-4-methyl-1-oxo-2S-(6-oxo-5S-1,7-diazaspiro[4.4]nonan-7-yl)pentyl]-L-tryptophanamide, MH+ 1216, 71% pure by h.p.l.c.

EXAMPLE 38

N-[N$^1$-[L-phenylalanyl]-4-methyl-1-oxo-2S-(6-oxo-5S-1,7-diazaspiro[4.4]nonan-7-yl)pentyl]-L-tryptophanamide, MH+ 587, 80% pure by h.p.l.c.

According to the general methods described above the following compounds were prepared:

EXAMPLE 39

N-[N$^1$-[N-(1,1-dimethylethoxy)carbonyl]-L-lysyl-L-phenylalanyl-L-tyrosyl]-4-methyl-1-oxo-2S-(6-oxo-5S-1,7-diazaspiro[4.4]nonan-7-yl)-pentyl]-L-tryptophanamide, trifluoroacetate salt, MH+ (T.O.F.)* 978, 95% pure by h.p.l.c.

EXAMPLE 40

N-[N$^1$-[N-(acetyl)-L-lysyl-L-phenylalanyl-L-tyrosyl]-4-methyl-1-oxo-2S-(6-oxo-5S-1,7-diazaspiro[4.4]nonan-7-yl)pentyl]-L-tryptophanamide, trifluoroacetate salt, MH+ (T.O.F.)* 919.7, 95% pure by h.p.l.c.

EXAMPLE 41

N-[N$^1$-[L-tyrosyl-L-phenylalanyl-L-tyrosyl]-4-methyl-1-oxo-2S-(6-oxo-5S-1,7-diazaspiro[4.4]nonan-7-yl)pentyl]-L-tryptophanamide, trifluoroacetate salt, MH+ (T.O.F.)* 884, 99% pure by h.p.l.c.

EXAMPLE 42

N-[N$^1$-[N-(1,1-dimethylethoxy)carbonyl]-L-glutaminyl-L-lysyl-L-phenylalanyl-L-tyrosyl]-4-methyl-1-oxo-2S-(6-oxo-5S-1,7-diazaspiro[4.4]nonan-7-yl)pentyl]-L-tryptophanamide, MH+ 1106, 96% pure by h.p.l.c.

EXAMPLE 43

N-[N$^1$-[pyroglutamyl-L-prolyl-L-lysyl-L-prolyl-L-glutaminyl-L-glutaminyl-L-phenylalanyl-L-phenylalanyl]-4-methyl-1-oxo-2S-(6-oxo-5S-1,7-diazaspiro[4.4]nonan-7-yl)pentyl]-L-tryptophanamide, MH+ (T.O.F.)* 1424, 97% pure by h.p.l.c.

*T.O.F.=time of flight

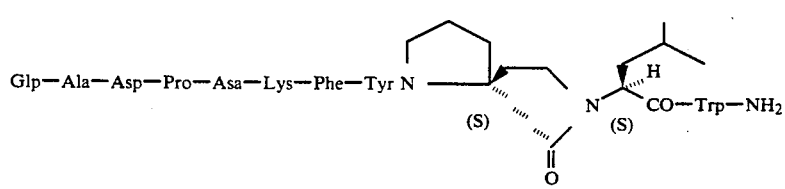

We claim:

1. Spirolactam derivatives of general formula (XI)

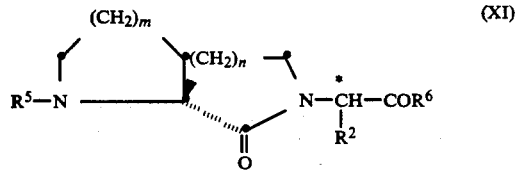
(XI)

wherein

R$^2$ represents the side chain of any naturally occurring amino acid;

n represents 1 or 2;

m represents 1 or 2;

the configuration at * may be (R) or (S) or a mixture thereof;

R$^5$ represents a peptide chain, optionally protected at the N-terminal residue, consisting of 2 to 8 amino acid units chosen from L-phenylalanine, D-phenylalanine, L-proline, L-glutamine, L-arginine, L-lysine, L-threonine, L-histidine, L-asparagine, L-methionine, D-methionine, L-alanine, L-serine, L-tyrosine, L-pyroglutamic acid, L-aspartic acid,

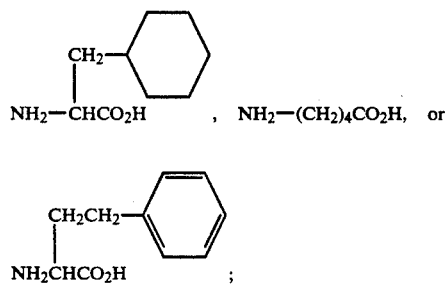

R$^6$ represents an amino acid amide chosen from L-methionyl,

D-methionyl, L-phenylalanyl or L-tryptophyl amides, optionally substituted on the amide nitrogen by the group —CH$_2$CH$_2$NH$_2$; or the groups

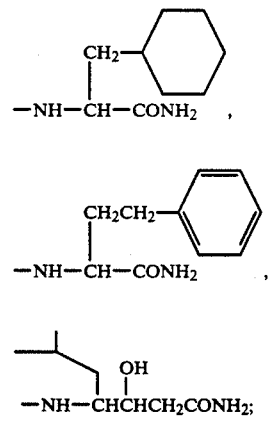

or R$^6$ represents the group

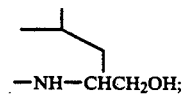

and solvates and acid addition salts thereof.

2. A pharmaceutical composition comprising a compound of formula (XI) as defined in claim 1 or a physiologically acceptable salt thereof in admixture with a pharmaceutically acceptable carrier, diluent or excipient.

3. A spirolactam derivative according to claim 1 which is